United States Patent [19]

Kramer

[11] 4,357,481

[45] Nov. 2, 1982

[54] ADAMANTANE CATALYZED PARAFFIN-OLEFIN ALKYLATION

[75] Inventor: George M. Kramer, Berkeley Heights, N.J.

[73] Assignee: Exxon Research and Engineering Co., Florham Park, N.J.

[21] Appl. No.: 298,119

[22] Filed: Aug. 31, 1981

[51] Int. Cl.³ .......................... C07C 2/58; C07C 2/60; C07C 2/62

[52] U.S. Cl. ................................ 585/724; 585/725; 585/726; 585/727; 585/728; 585/729; 585/730; 585/731; 585/732; 585/721; 585/723

[58] Field of Search ............... 585/724, 725, 726, 727, 585/728, 729, 730, 731, 732

[56] References Cited

U.S. PATENT DOCUMENTS

| | | | |
|---|---|---|---|
| 2,965,693 | 12/1960 | Kramer | 585/728 |
| 3,231,633 | 1/1966 | Kramer | 585/723 |
| 3,324,196 | 6/1967 | Kramer et al. | 585/725 |
| 3,382,288 | 5/1968 | Schneider | 585/352 |
| 3,546,308 | 12/1970 | Moore | 585/352 |
| 3,551,514 | 12/1970 | Evering | 585/731 |
| 3,671,598 | 6/1972 | Moore | 585/350 |
| 3,689,590 | 9/1972 | Rakow et al. | 585/731 |
| 4,162,233 | 7/1979 | Kramer | 252/429 R |
| 4,229,611 | 10/1980 | Kramer | 585/728 |

OTHER PUBLICATIONS

"Industrial Laboratory Alkylation" edited by Lyle F. Albright and Arthur R. Goldsby, ACS Symposium Series 55, published Washington, D.C., 1977, Chapter One, "Alkylation Studies" by George M. Kramer.

J. Org. Chem. 44, pp. 2619-2624 (1979), by D. Mirda, D. Rapp and G. M. Kramer.

J. Amer. Chem. Soc. 98, pp. 5864-5870, (1976), by P. Van Pelt and H. M. Buck.

Primary Examiner—Curtis R. Davis
Attorney, Agent, or Firm—Robert J. North

[57] ABSTRACT

A process is described for paraffin-olefin alkylation under strong acid conditions in which an adamantane hydrocarbon is used to substantially increase the reaction rate of the alkylation.

12 Claims, No Drawings

ADAMANTANE CATALYZED PARAFFIN-OLEFIN ALKYLATION

BACKGROUND OF THE INVENTION

This invention relates to a process for paraffin-olefin alkylation producing highly branched paraffins under strong acid catalyzed conditions and in the presence of adamantane hydrocarbons as hydride transfer catalysts.

Alkylation of olefins by carbonium ions under strong acid conditions is a well-known process for producing a wide variety of useful hydrocarbon materials and particularly, gasoline additives. For example, trimethylpentanes are common additives used for blending into gasoline for octane improvement which can be produced by alkylating isobutylene with isobutane in sulfuric acid or liquid HF. An example of an acid catalyzed reaction process is described in U.S. Pat. No. 3,231,633.

Hydrocarbon conversion processes employing novel Lewis acid systems are disclosed in U.S. Pat. No. 4,229,611 and 4,162,233, both assigned to Exxon Research and Engineering Company.

U.S. Pat. No. 3,671,598 describes a process for isomerizing saturated cyclic hydrocarbons under strong acid conditions in the presence of an adamantane hydrocarbon. However, no suggestion is made that an adamantane compound might be useful in paraffin-olefin alkylation under strong acid conditions.

New methods for producing alkylated paraffinic hydrocarbons useful as octane improvement agents are constantly being searched for in an effort to increase product quality, yield and reaction rate, while lowering acid consumption and decreasing the cost of said process.

SUMMARY OF THE INVENTION

We have unexpectedly found that the presence of an adamantane hydrocarbon in a strong acid system containing alkyl or paraffinic carbonium ions increases the rate of intermolecular hydride transfer between paraffins and carbonium ions in the system. Since intermolecular hydride transfer is generally the rate determining step in paraffin-olefin alkylation, (see "Industrial Laboratory Alkylation", edited by Lyle F. Albright and Arthur R. Goldsby, ACS Symposium Series 55, published Washington, D.C., 1977, Chapter One, "Alkylation Studies", by G. M. Kramer) involving paraffinic carbonium ions, then the presence of the adamantane hydrocarbon will serve to significantly increase the reaction rate of the alkylation process. In the production of octane-increasing agents, this should lead to the formation of purer product quality due to higher selectivity, lower acid consumption, which is an environmental consideration, and higher yields, which enhances the economics of the process. In the case of butene alkylation, better product quality means the production of alkylate containing higher percentages of $C_8$ compounds, and these contain more trimethylpentane than poorer quality alkylate.

More specifically, by this invention, there is provided an alkylation process comprising contacting a $C_4$–$C_6$ linear or branched paraffinic compound, capable of forming a carbonium ion under strong acid conditions, with a $C_2$–$C_5$ olefin in the presence of a strong acid system and an adamantane hydrocarbon containing at least one unsubstituted bridgehead position, at a temperature of about $-100°$ to $150°$ C., thereby producing a $C_6$–$C_{11}$ branched paraffinic hydrocarbon.

In the process, the total range of described applicable paraffins and olefins can be used in the subject paraffin-olefin alkylation process under very strong acid conditions, e.g., $AlBr_3$. However, in the slightly weaker acid systems, such as $H_2SO_4$ and HF, ethylene and n-butane do not generally undergo the alkylation process and require the stronger acid systems, as described herein.

DESCRIPTION OF THE INVENTION AND PREFERRED EMBODIMENTS

The reason that adamantane hydrocarbon serves to increase the rate of intermolecular hydride transfer during paraffin-olefin alkylation, is not clearly understood. One theory that we do not wish to be bound by is that hydride transfer from adamantane to a carbonium ion in solution is enhanced due to lack of steric repulsions in the transition state involving adamantane during the process, as compared to that involving a paraffinic hydrocarbon.

In the process, $C_2$–$C_5$ olefins are alkylated by $C_4$–$C_6$ linear or branched paraffinic compounds to produce effective gasoline octane improvement agents. Preferably, the starting paraffinic compound used is branched, since branching facilitates reaction and results in a higher octane number product for combustion purposes. Representative examples include n-butane, isobutane, n-pentane, isopentane, n-hexane, 2- and 3-methylpentanes and the like. A preferred paraffin hydrocarbon in the process is isobutane.

Carbonium ions in the process can be generated in various ways; most often by protonation of an olefin, but also by oxidation of a paraffin or in situ from their respective halides, e.g., t-butyl chloride, in the acid system, or they can be generated from the free hydrocarbon by undergoing intermolecular hydride transfer with in situ generated adamantyl cation. The preferred method depends on the acid system, but in $H_2SO_4$ or HF, they are readily formed by protonation of olefins.

Linear or branched $C_2$–$C_5$ olefins useful in the process include ethylene, propylene, butene-1, cis or trans butene-2, isobutylene, pentene-1, pentene-2, methylbutenes, mixtures thereof, and the like. Preferred olefins are butylenes.

Weight ratio of paraffin-olefin used in the process is generally about 5 to 1 and preferably about 10 to 1.

The product hydrocarbons in the reaction of isobutane with butylenes are mainly $C_8$ branched paraffins. Representative examples include 2,2,4-, 2,3,4-, 2,3,3- and 2,2,3-trimethylpentanes, 2,4-, 2,3- and 2,5-dimethylhexanes and the like. Preferred products in the process are the trimethylpentanes.

The phrase "a strong acid system", as used herein, refers to an acid system capable of assisting in generating carbonium ions in the process and includes an "acid component" and a solvent, or a material that can function in both capacities such as concentrated sulfuric acid or liquid HF. The acid system can be a solid, liquid, gas or vapor. Preferred is a liquid acid system.

The strong acid components in the acid system are conventional protic, aprotic or Lewis acids and include $AlBr_3$, $AlCl_3$, $GaCl_3$, $TaF_5$, $AsF_5$, $BF_3$, HF, HCl, HBr, $H_2SO_4$, $HSO_3F$, $CF_3SO_3H$, and the like, and mixtures thereof. Preferred acid components in the process are $H_2SO_4$, HF, $HSO_3F$ and $CF_3SO_3H$.

Also a component of the "acid system" is a solvent for the acid components. For Lewis acids, halogenated paraffins and aromatics are generally used; representative examples include $CH_3Br$, $CH_2Br_2$, $CH_2Cl_2$, 1,2-dichloroethane, 1,2,3-trichlorobenzene, 1,2,3,4-tetrachlorobenzene, pentafluorobenzene, HF, $H_2SO_4$, $CF_3SO_3H$, and the like, and mixtures thereof.

The molar concentration of acid component in solvent, if they are different materials, is generally between 0.1 and 8.0 M, and preferably between 0.5 and 4.0 M (moles/liter).

The volume ratio of the acid system to the paraffinic hydrocarbon is generally about 5/1 to 1/5 and preferably 3/1 to 1/3. However, larger and smaller ratios can also be effectively employed.

The adamantane hydrocarbon useful in the process contains from zero to four linear or branched alkyl groups and contains at least one unsubstituted bridgehead position and can be prepared by conventional methods in the art. It is believed that at least one bridgehead adamantane position must be unsubstituted in order for an increase in intermolecular hydride transfer to occur. The adamantyl ring can be substituted with alkyl groups which are generally linear or branched $C_1-C_4$ alkyl moieties, being methyl, ethyl, n-propyl, isopropyl, n-butyl, isobutyl, t-butyl, and the like. A preferred alkyl substitute, if present, is methyl.

Representative adamantane hydrocarbons in the process are adamantane, 1-methyl-adamantane, 2-methyl-adamantane, 1,3-dimethyl-adamantane, and the like. Preferably unsubstituted adamantane is used.

The molar concentration of adamantane hydrocarbon in solution in the paraffinic hydrocarbon in the process ranges from about 0.1 to 1.0 M (moles/liter). However, larger and smaller ratios can also be used effectively.

The process is conducted at temperatures in the range of about $-100°$ to $150°$ C. and preferably about $-65°$ to $65°$ C.

The process is normally carried out at atmospheric pressure, but may also be conducted at higher pressures up to about 20 atmospheres.

Yields of alkylate in the process range from about 150 to 204 percent of theory based on starting olefin, (butylene).

$$\text{Yield} = \left(\frac{\text{weight of product}}{\text{weight of olefin fed}}\right) \times 100$$

Particularly preferred embodiments of the process are where: butylenes are reacted with isobutane to produce an alkylate comprising at least 80 weight percent trimethyl pentanes; propylene is reacted with isobutane to produce a $C_7$ hydrocarbon mixture which is mainly 2,3- and 2,4-dimethylpentane; and wherein the $C_3$, $C_4$, $C_5$ olefin streams used in the alkylation are obtained from catalytic cracking.

Apparatus for carrying out the subject process is conventional, either on a laboratory, pilot plant, or full industrial scale, and the process can be conducted in a batch-type operation or in a continuous-type operation, and in a slurry, liquid, gaseous, or vapor phase. Preferred is a continuous process.

Generally, the process is conducted by contacting a liquid mixture of paraffin, olefin and adamantane hydrocarbon with the acid system described herein. If the hydrocarbon mixture is miscible with said acid system, then the reaction takes place in a one-phase homogeneous manner. If the acid system is, for example, $H_2SO_4$, then the process is conducted in a two-phase manner, the acid system being the lower phase. The entire system is preferably at reaction temperature at time of mixing during which the entire system is adequately mixed, stirred and agitated to insure good contact between the acid system and the hydrocarbon system. The reaction is allowed to progress until a desired or substantial quantity of formed product is obtained. This can be monitored by analytical methods such as gas chromatography and mass spectrometry. After the desired paraffinic product has been formed, the phases can be separated and the hydrocarbon phase treated by extraction or fractional distillation, and the like, to separate out and collect the desired product. The adamantane hydrocarbon can be recovered and recycled back to the reactor for further use.

It is to be understood that obvious modifications and variations on the above-described procedure and subject process not specifically described herein, are deemed to be encompassed within the general scope and spirit of this application.

The following example is illustrative of the best mode of carrying out the invention as contemplated by me, and should not be construed as being limitations on the scope or spirit of the instant invention.

EXAMPLE

Aluminum bromide solutions were prepared by weighing 0.534 grams (0.002 moles) $AlBr_3$ (purified by sublimation), into an NMR tube. The tube was cooled to $-80°$ C. and then gaseous $CD_3Br$ was passed through a bed of $CaCl_2$ (drier), and condensed as a liquid on the $AlBr_3$ to provide a half milliliter of a four molar solution. The mixture was warmed and shaken quickly to provide the solution for study.

A t-butyl cation-adamantane system used in the study was prepared by two different methods. One method was by adding t-butylbromide and adamantane to the acid mixture just before warming and shaking to insure reaction. The other method was by reversing the first procedure and mixing 1-bromoadamantane with isobutane. The additive concentrations were 0.1 M in both cases and provided clear homogeneous solutions.

Proton nuclear magnetic resonance studies were done at $-40°$ C. on a Varian 360-L spectrometer. Both solutions exhibited similar spectra showing sharp absorption bands for the butyl methyl groups and another sharp absorption band for the methylene protons of adamantane.

However, solutions of t-butyl cation with isopentane, norbornane and methylcyclopentane, prepared in similar manner, as described above, exhibited a much broader band for the butyl system protons at similar conditions, indicating that much slower intermolecular hydride transfer was occurring in these systems in the absence of dissolved adamantane.

Thus, in a paraffin-olefin acid catalyzed alkylation process, such as between isobutane and isobutylene, propylene, butylenes and amylenes in which intermolecular hydride transfer is known to be the rate determining step, the presence of adamantane increases the reaction rate.

Thus, it is reasonably believed that in a paraffin-olefin acid catalyzed alkylation process, such as between isobutane and isobutylene, in which intermolecular hydride transfer is known to be the rate-determining step, the presence of adamantane hydrocarbon will substantially increase the reaction rate.

Another particularly preferred embodiment which we, not described herein above is wherein the paraffinic compound is isobutane and the olefin is a mixture of amylenes and the product comprises a mixture of branched $C_8$ and $C_9$ paraffinic hydrocarbons.

What is claimed is:

1. An alkylation process comprising contacting a $C_4$–$C_6$ linear or branched paraffinic compound capable of forming a carbonium ion under strong acid conditions, with a $C_2$–$C_5$ olefin, in the presence of a strong acid system and an adamantane hydrocarbon containing at least one unsubstituted bridgehead position, at a temperature of about $-100°$ to $150°$ C., thereby producing a $C_6$–$C_{11}$ branched paraffinic hydrocarbon.

2. The process of claim 1 wherein said paraffinic compound is selected from n-butane, isobutane, n-pentane, isopentane, n-hexane, 2-methylpentane, isomers thereof, and mixtures thereof.

3. The process of claim 1 wherein said olefin is selected from ethylene, propylene, butene-1, cis or trans butene-2, isobutylene, pentenes, isomers thereof, and mixtures thereof.

4. The process of claim 1 wherein said acid system contains an acid component selected from $AlBr_3$, $AlCl_3$, $GaCl_3$, $TaF_5$, $AsF_5$, $BF_3$, HF, HCl, HBr, $H_2SO_4$, $HSO_3F$, $CF_3SO_3H$, and mixtures thereof.

5. The process of claim 4 wherein said acid component is HF, $H_2SO_4$, $HSO_3F$, or $CF_3SO_3H$.

6. The process of claim 4 wherein said acid system further contains a solvent selected from $CH_3Br$, $CH_2Br_2$, $CH_2Cl_2$, 1,2-dichloroethane, 1,2,3-trichlorobenzene, 1,2,3,4-tetrachlorobenzene pentafluorobenzene, HF, $H_2SO_4$, $HSO_3F$, $CF_3SO_3H$, and mixtures thereof.

7. The process of claim 1 wherein said adamantane hydrocarbon is unsubstituted adamantane.

8. The process of claim 1 wherein said temperature is in the range of about $-65°$ to $65°$ C.

9. The process of claim 1 being conducted in a continuous manner.

10. The process of claim 1 wherein said paraffinic compound is isobutane, said olefin is a mixture of butenes and said product is an alkylate, comprising $C_8$ hydrocarbons of which trimethylpentanes are at least 80 weight percent.

11. The process of claim 1 wherein said paraffinic compound is isobutane, said olefin is propylene and said $C_7$ product is predominantly a mixture of 2,3- and 2,4-dimethylpentanes.

12. The process of claim 1 wherein said paraffinic compound is isobutane, said olefin is a mixture of amylenes, and said product comprises a mixture of branched $C_8$ and $C_9$ paraffinic hydrocarbons.

* * * * *